United States Patent
Wu et al.

(10) Patent No.: US 8,313,955 B2
(45) Date of Patent: Nov. 20, 2012

(54) DEVICES AND METHODS FOR DETECTING ANALYTES

(75) Inventors: Xin Wu, Hangzhou (CN); Fuquan Zhao, Hangzhou (CN); Yinfei Wu, Hangzhou (CN); Fei Gao, Hangzhou (CN)

(73) Assignee: Alere Switzerland GmbH, Zug (CH)

( * ) Notice: Subject to any disclaimer, the term of this patent is extended or adjusted under 35 U.S.C. 154(b) by 378 days.

(21) Appl. No.: 12/531,532

(22) PCT Filed: Mar. 17, 2008

(86) PCT No.: PCT/IB2008/001677
§ 371 (c)(1),
(2), (4) Date: Feb. 12, 2010

(87) PCT Pub. No.: WO2008/135862
PCT Pub. Date: Nov. 13, 2008

(65) Prior Publication Data
US 2010/0143941 A1   Jun. 10, 2010

(30) Foreign Application Priority Data
Mar. 16, 2007 (CN) .......................... 2007 1 0067607

(51) Int. Cl.
*G01N 33/558* (2006.01)

(52) U.S. Cl. ......... 436/514; 422/420; 422/425; 435/7.1; 435/7.5; 435/7.93; 435/7.94; 435/970; 436/518

(58) Field of Classification Search ................... 435/7.1, 435/7.5, 7.93, 7.94, 970; 436/514, 518; 422/420, 422/425
See application file for complete search history.

(56) References Cited

U.S. PATENT DOCUMENTS

| | | | |
|---|---|---|---|
| 4,806,312 A | | 2/1989 | Greenquist |
| 5,451,504 A | * | 9/1995 | Fitzpatrick et al. ............ 435/7.2 |
| 6,306,665 B1 | * | 10/2001 | Buck et al. .................... 436/530 |
| 6,706,539 B2 | * | 3/2004 | Nelson et al. ................ 436/514 |
| 2002/0142291 A1 | | 10/2002 | Bauer et al. |

FOREIGN PATENT DOCUMENTS

| | | |
|---|---|---|
| WO | WO 93/03175 | 2/1993 |
| WO | WO 97/31269 | 8/1997 |
| WO | WO 2005/059547 | 6/2005 |

OTHER PUBLICATIONS

International Search Report (ISR) from PCT/IB2008/001677.

* cited by examiner

*Primary Examiner* — Chris L Chin
(74) *Attorney, Agent, or Firm* — DLA Piper LLP (US)

(57) ABSTRACT

This invention provides devices and methods for detecting an analyte suspected to be present in a sample. The subject devices and methods are particularly useful for performing immunoassays on a variety of analyte, especially those present in a bodily fluid.

23 Claims, 7 Drawing Sheets

DEVICES AND METHODS FOR DETECTING ANALYTES

BACKGROUND OF THE INVENTION

Immunoassays for detecting an analyte in a sample are used extensively in various fields. Immunoassays can be used to detect analytes in various samples (such as saliva, blood, urine, serum, and sweat) to aid in diagnosis, prognosis and/or treatment of diseases. For instance, immunoassays are routinely performed for monitoring signs of early pregnancy, the presence of tumors, infectious diseases and drug abuse. Immunoassay is effected by the specific binding sites contained between immune molecules, such as antigen/antibody, hapten/antibody, and biotin/antibiotin. Most immunoassays are performed on a solid phase, such as on lateral-flow test strips, glass or plastic multi-porous discs, or immune chromatography devices.

There are two common formats of immunoassays, namely the sandwich assay and the competitive assay. In a competitive immunoassay, the analyte competes with a labeled analyte to bind with antibodies. This format has been commonly used to detect small analytes such as hapten in a sample. The label used can be one that indicates its presence as a color band in the detection or result reading zone. Reagents and devices utilizing competitive principle have been described in detail in U.S. Pat. Nos. 4,235,601, 4,442,204, 5,229,073. For devices utilizing competitive principles, if the color of the detection zone does not change or if no color band appears in detection zone or result reading zone, this indicates a positive result, and thus suggests that an analyte may be present in a sample. Conversely, if color is already present in the detection zone or result reading zone changes or if a color band appears, this can be interpreted as a negative result, which further suggests that the analyte may not be present in a sample.

Other devices in which a positive result is directly indicated have been described in, for example, U.S. Pat. Nos. 5,028,535, 5,089,391, 5,627,526, 5,143,852, 5,480,792, and 5,985,579. When such a device is used to detect, for example, hapten, if the analyte is present or if its concentration is higher than an anticipated threshold, the color appearing in the test zone suggests a positive result. Conversely, a negative result suggests analyte may not be present or that the analyte concentration is lower than an anticipated threshold. Although the above-mentioned devices and methods can detect several analytes at one time, there are still many disadvantages to the current devices available. For instance, samples and multiple antibodies for binding analytes have to be put in a sample well for about 10-15 minutes to react prior to be applied to the nitrocellulose (NC) membrane. Furthermore, the NC membrane has to be washed repetitively prior to reading the results. Thus such devices are time-consuming, inconvenient to operate, and require multi-steps reactions.

In U.S. Pat. No. 5,451,504 a test strip is disclosed comprising three specific zones, a mobilization zone, a trap zone and a detection zone. An antibody, bound to a color label in the mobilization zone, can bind with an analyte to form a complex (a color label-antibody-analyte complex). The complex can be moved by a liquid to a trap zone where a ligand is immobilized. The immobilized ligand is not able to bind to an antibody that has already formed a complex with an analyte. Such a complex is stable and cannot be affected by the immobilized ligand. The ligand can only bind an antibody that is freely floating and not already bound to an analyte. The analyte-antibody complex can then be captured by an immobilized detection receptor as to show a direct positive result. However, the device described in this patent requires that the affinity between the antibody and the analyte be higher than the affinity between the antibody and the ligand. In practice, it is very difficult to select the antibody with these limited features to apply to this invention.

In U.S. Pat. No. 6,699,722 a test strip is described consisting of a sample application zone, a mobilization zone, a first capture zone and a second capture zone. In this device, these zones are arranged along the pathway of liquid flowing, so that the liquid flows through each zone sequentially. The first capture zone is coated with a first capture antibody and the second capture zone is coated with a second capture antibody. The molecular weight of a labeled analyte analog is heavier than the weight of the analyte in the sample. If an analyte is present in the sample, the labeled analyte analog and analyte will move along following the pathway of the flowing liquid with the analyte traveling faster than the analyte analog. As result, the analyte will reach the first capture zone earlier than labeled analyte analog. The analyte is captured and fixed by the first capture antibody before the labeled analyte analog reaches the capture zone. The, labeled analyte analog will continue to flow past the first capture zone and come in contact with the second capture zone coated with a second capture antibody. The color in second capture zone will then change in response to the binding of the labeled analyte analogs further indicates a positive result. In practice, such a test strip is inconvenient and the results from such a test strip are not accurate.

SUMMARY OF THE INVENTION

The present invention provides a test device for detecting the presence or absence of an analyte in a liquid sample. The test device typically comprises a mobilization zone comprising a mobilizeable ligand and a mobilizeable antibody, wherein the mobilizable antibody specifically binds the analyte and/or the mobilizeable ligand; a blocking zone located downstream from the mobilization zone, wherein the blocking zone comprises an immobilized trapping receptor that binds the mobilizeable ligand; and a detection zone located downstream from the blocking zone, wherein the detection zone comprises an immobilized detecting receptor that binds the mobilizeable antibody. In one embodiment, the mobilizeable antibody is adapted to be contacted by the sample before the mobilizeable ligand is contacted by the sample. In another embodiment, the mobilizeable ligand is adapted to be spatially separated from the mobilizeable antibody so that the sample contacts the mobilizeable antibody prior to contacting the mobilizeable ligands. Where desired, the device of claim can be configured to adopt a lateral flow strip format that supports a flow of said liquid sample across the mobilization zone, the blocking zone, and the detection zone. In some embodiments, the mobilizeable ligand and the mobilizeable antibody are adapted to be separated by a gap. In some embodiments, the mobilizeable ligand and the mobilizeable antibody are adapted to be separated from each other a vertical or horizontal distance. In other embodiments, the mobilizeable ligand comprises a member of a binding pair that is distinct from the analyte, and wherein the immobilized trapping receptor comprises other member of the binding pair. The binding pair can be selected from the group of biotin and avidin, biotin and streptoavidin, and rhodamine and anti-rhodamine. In yet other embodiments, the mobilizeable antibody exists in a dry state and is contained in a first bibulous strip, and the mobilizeable ligand exists in a dry state and is contained in a second bibulous strip; and wherein the first strip is physically separated from the second strip. In still yet other embodiments, the blocking zone and detection zone are located on the second bibulous strip, downstream from the mobilizeable ligand.

In some embodiments, the mobilizeable antibody and the mobilizeable ligand exhibit a first binding affinity, and the analyte and the mobilizeable antibody exhibit a second binding affinity, wherein the first binding affinity is higher than the second affinity constant. The mobilizeable antibody can further comprise a color particle. In some other embodiments, the mobilizeable ligand and mobilizeable antibody are configured on the mobilization zone so that contact time during which the sample contacts the mobilizeable antibody is longer than contact time during which the sample contacts the mobilizeable ligand. Where desired, the mobilizeable antibody comprises a detectable label.

The present invention also provides methods of using the subject device. In one embodiment, the present invention provides a method for detecting the presence or absence of an analyte in a liquid sample by contacting the liquid sample with a subject test device (any one of which described herein) to effect detecting the presence or absence of said analyte. In one embodiment, the subject method proceeds with contacting the liquid sample with mobilizeable antibody on the test device to form a first mixture, followed by contacting the first mixture with the moblizeable ligand to form a second mixture, wherein the second mixture further makes contact with the blocking zone.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
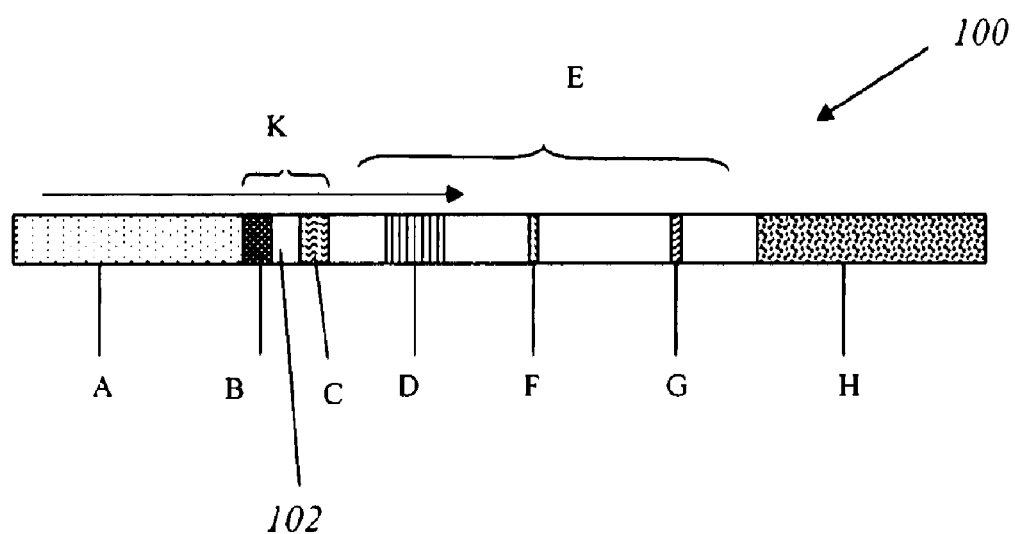
FIG. 1 is an illustration of a test strip of the device.

The devices and methods described are adapted and configured to detect the presence or absence of an analyte by directly providing a positive or negative result. Typically, a test device is a test strip comprising a mobilization zone K, blocking zone D and detection zone F, e.g., as shown in FIG. 1. The mobilization zone comprises a mobilizeable ligand and a mobilizeable antibody for specifically binding either a target analyte or the mobilizeable ligand. A trapping receptor for capturing the mobilizeable ligand, is present in the blocking zone D. Typically, the trapping receptor can capture the ligands but not directly capture any analyte-binding antibody. The detection zone of the device further comprises an immobilized detecting receptor which can bind to the mobilizeable antibody, for example after the antibody has been dissolved into solution. In some embodiments, the test strip comprises a bibulous material for supporting a fluid sample flowing thereon. A bibulous material refers to those materials that can stably absorb a fluid and make the fluid pass through the material via capillary action. In some embodiments, a bibulous material can be a material that supports the movement and transport of fluids along its length. In another embodiment, the bibulous material is a material for driving fluid movement through the device via capillary action. The test strip may comprise a single type of bibulous material on which the antibodies and ligands are disposed. Alternatively, the test strip can be made up of multiple kinds of bibulous materials which can act reciprocally together with a fluid sample. Bibulous materials include, but are not limited to, nitrocellulose, filter paper, fiberglass, polyester. In addition, the bibulous solid phase, in some embodiments, further contains other suitable reagents for conducting the test on the device. By way of example only, the solid phase may further contain a buffer solution to adjust pH value.

The test strip of the test device further comprises a sample application zone A for receiving the sample. The application zone A is located upstream of a blocking zone D, an absorbent zone H for absorbing the sample after it has passed through the test strip, and a test control zone G. The test control zone comprises an amount of reagent for determining if the sample has had enough time to pass over the detection zone, or if enough time to complete the test has passed. When the test device is used, an amount of antibodies specifically binding to either a target analyte or an amount of ligand are contained on the analyte binding zone of the mobilization zone. The antibodies can be in a dry state. The mobilization zone further has an amount of the ligands located in the regulation zone of the mobilization zone. The ligands are located downstream of the analyte binding antibodies.

The antibodies and ligands can be dissolved by the sample. In their dissolved state, the antibodies and ligands move through the zones of the test device with the sample, as the sample passes through the corresponding zones. In some embodiments, in the test device, a sample first contacts the antibodies located in the antibody binding zone of the mobilization zone. The antibodies are dissolved in the sample and come in contact with the analyte in the sample. The sample remains in contact with the antibodies in the antibody binding zone for a period of time. The time period is sufficient to form a first liquid mixture consisting of the analyte bound to antibodies, or an analyte-antibody complex. In some embodiments, all of the analyte-binding antibodies are dissolved in the sample. In some embodiments, at least a portion of analyte-binding antibodies is dissolved in the sample. The first liquid mixture then passes to the regulation zone, located subsequent to the analyte binding zone, where the first liquid mixture comes into contact with the ligands located in the regulation zone. The ligands are then dissolved by the first liquid mixture further forming a second liquid mixture. In some embodiments, the sample does not contain any target analyte. In such an embodiment, the mobilized antibodies carried in the first mixture can be bound by the mobile ligands dissolved in the second liquid mixture, so as to form antibody-ligand complexes. These antibody-ligand complexes can then be captured by an amount of trapping receptors located in the blocking zone. The trapping receptors are ligands located in the blocking zone have specific binding sites for directly binding the mobilized ligands. The trapping receptors are immobilized on the blocking zone located downstream of the mobilization zone. Because the antibody-ligand complexes are bound by the trapping receptors, the mobilized antibodies generally do not pass through the blocking zone. Typically, any unbound ligands dissolved in the second liquid mixture will subsequently be bound by the trapping receptors on the blocking zone as well.

If an analyte or an amount of analyte is present in the sample, at least a portion of the analyte can be bound by the mobilizeable antibodies on the analyte binding zone. If present the analytes typically form a first complex, an antibody-analyte complex, to create a first liquid mixture. In some embodiments, only a portion of the analyte binding antibodies are bound by the target analyte. In such an embodiment, the antibodies dissolved in the first liquid mixture, but which remain unbound to an analyte, can then be bound by the ligands located in the regulation zone. When the first liquid mixture contacts the ligands located downstream of the antibody binding zone, a second mixture is formed. The second mixture typically includes the first antibody-analyte complexes and the ligands dissolved by the first liquid mixture.

In some embodiments, all of the antibody-analyte complexes remain undisturbed by the dissolved ligands. In some embodiments, some of the dissolved ligands will compete with the analyte to bind to the binding sites on the antibodies of the first complexes. In such a case, the first liquid mixture can contain both analyte-antibody complexes and antibody-ligand complexes. The second mixture then comes in contact with the blocking zone. The blocking zone typically contains an amount of immobilized trapping receptors. The trapping receptors can bind to either the ligand-antibody complex, if a portion of the antibodies are unbound by the analytes, or to unbound ligands, if only a portion of the ligands are bound to the mobilized antibodies. The trapping receptors typically do not capture the antibody-analyte complexes.

The sample then passes to the detection zone, located downstream from the blocking zone. The analyte-antibody complexes can, in some embodiments, be captured by an amount of detection molecules immobilized on the detection zone of the test device when the second liquid mixture arrives at the detection zone. The detection zone has an amount of immobilized receptors for specifically binding the analyte binding antibodies. The receptors are typically antibodies. In some embodiments, the analyte-binding antibodies are conjugated with a detectable label. Determining the amount of the detectable label correlates to the amount of the anlayte in the test sample. Typically, the detectable labels are color particles. The amount of the analyte can then be directly determined through detecting the color particles captured on the detection zone by naked eyes.

When the second liquid mixture comes in contact with the detection zone, specific binding sites on the antibody are typically exposed when dissolved in the sample. The exposed binding sites of the antibodies are typically recognizable by the analyte, so as to enable a reaction in a substantially short period of time. The second liquid mixture contains the ligands dissolved in the sample. In some embodiments, the ligands dissolved in the sample compete with the analyte for the antibodies already complexed with the analyte. Alternatively the ligands may bind to any unbound analyte-binding antibodies directly, since the binding sites of the ligands are also exposed when the ligands are dissolved in the first mixture. Further, in some other embodiments, the ligand is directly or indirectly connected to, linked with, or conjugated with one member of a binding pair of specific molecules that are not related to the analyte-binding antibody. In such an embodiment, some of the binding sites of the ligands are covered by one member of the pair. This configuration reduces the competition between the ligand and the analyte for the binding site on the antibodies in the antibody-analyte complex. In some embodiments, the ligand comprises a portion of a conjugate that includes biotin. The ligand further forms a biotin/avidin conjugate, wherein the avidin is immobilized on the blocking zone for capturing the second complexes (antibody-ligand-biotin) when the second mixture passes through the blocking zone. In yet another embodiment, the ligands are a portion of a conjugate with one partner of a pair of specific binding molecules conjugated with a protein.

In modern assays for small molecules, especially for drug abuse detection, the lowest concentration, or the cut-off value, should be changed in order to distinguish drug abusers from patients undergoing normal medical treatment. For example, if a patient's blood is analyzed for presence of an analyte, the patient blood may contain a concentration of an analyte higher than the standard cut-off value. When the concentration of the target analyte in a sample is higher than the standard cut-off value, that may not necessarily mean that the patient is a drug user. The patient may simply have a higher concentration of analyte simply due to the fact that he/she consumes the analyte as part of treatment. In such a situation, the concentration of the analyte can not be detected by the device and compared with the standard level of the analyte in the general population. It would be more accurate to use a device with an increased cut-off value to identify a potential drug user. In some embodiments, the device comprises an analyte binding antibody located in the mobilization zone, wherein the antibody has a lower affinity, $K_1$, for binding a target analyte than its affinity, $K_2$, for binding to the ligand. If $K_1$ is less than $K_2$, a higher concentration of analyte is required to compete with the mobilizeable ligand for the binding sites located on the mobilizeable antibody in the second liquid mixture. Thus, a proper negative result, not a false positive result, can result on the detection zone even if the analyte concentration is higher than a standard level in patient's body fluid. An antibody with an affinity of $K_1$ less than or equal to $K_2$ is typically used.

The antibody for specifically binding an analyte and the ligand may both be in a dry phase prior to being contacted by the liquid sample. Alternatively the antibody can be in the liquid phase prior to being contacted by a sample. The antibody and ligand are typically contained on the single strip of the test device in the dry state. When a liquid sample moves through the mobilization zone, the antibodies and the ligands can be dissolved in, and carried by, the liquid sample.

The mobilizeable antibody specifically capable of binding to an analyte can be conjugated with a detectable label. The label can be selected from, but not limited to, an enzyme, a non-water soluble particle, a colloidal gold particle, a latex particle, or any combination thereof. In some embodiments, the label is a water-soluble substance or a fluorescent substance. The label can be any label suitable for labeling the antibody.

The test device can be used to detect an analyte using the competition principle employed in immunoassays to indicate the presence or absence of a target analyte in a sample by displaying a direct positive or negative result. In particular, the subject device can comprise electronic readers that detects optical signals generated in an immunoassay.

I. DEVICES

FIG. 1 depicts one embodiment of the test device. The test device, as shown, comprises a test strip 100 having an sample reception zone A, an analyte binding zone B typically containing an amount of antibodies and color labels, a regulation zone C, with an amount of ligands as a portion of conjugates conjugated with biotin, and a nitrocellulose membrane E. The nitrocellulose membrane further comprises a blocking zone D, with an amount of immobilized avidin, a detection zone F, and a result control zone G. Typically, an absorption zone H, for absorbing the liquid passed from the mobilization zone K to the control zone G, is present. The mobilization zone K encompasses both the analyte-binding zone B and the regulation zone C. The analytes and ligands on the analyte binding zone and regulation zone, respectively, can be dissolved and carried along the test strip by the sample.

The sample reception zone A is typically located upstream from the mobilization zone. The sample reception zone A can, additionally, be treated with chemical reagents which can improve or regulate the reactive conditions between the analyte and the antibody. Chemical reagents used include, but are not limited to, reactive PH values, ionic concentrations, removal of some interferential substances in the samples, or any other suitable chemical reagent, or any combination thereof known in the prior art. The absorbent zone H is typically located downstream from the detection zone so as to facilitate and enhance the flow of liquid. Suitable materials for absorbent zone include, but may not be limited to, filter paper, or any other absorbent materials.

The mobilization zone K comprises an amount of antibodies for binding to either a target analyte or an amount of ligand. The antibodies are contained in the mobilization zone in a dry state. The mobilization zone further has an amount of the ligands thereon downstream from the analyte binding antibodies. The antibodies and ligands can be moved by and dissolved in the sample when the sample passes the corresponding zones. An amount of ligand can be contained on the regulation zone C located downstream from the analyte binding zone B. In addition, an amount of antibodies for specially binding the analyte can be contained in a dry state on the analyte binding zone B. A liquid sample is typically applied to the strip 100. The sample then comes in contact with the analyte binding antibody located on the analyte binding zone B for a period of time. The sample then comes into contact with the ligands on the regulation zone C for a time period shorter than the time period in which the sample was in contact with the analyte binding zone B. The analyte and analyte binding antibodies form a first mixture in the antibody binding zone, which can be maintained in the antibody binding zone for a period of time prior to contacting the ligands located downstream from the analyte binding antibodies. The time in which the first mixture typically contacts the analyte binding antibody is longer than the time in which the second mixture contacts the mobilizeable ligand. In some embodiments, the time in which the first mixture contacts the analyte binding antibody is between about one second to about sixty seconds. In some embodiments, the time is between about 10 seconds to about 30 seconds. In some embodiments, the time period is longer than 60 seconds.

The test strip typically further comprises an analyte binding zone B and a regulation zone C, with a gap 102 separating the analyte binding zone B and the regulation zone C. The gap 102 typically comprises a bibulous material. In some embodiments of the device described herein, more than one gap is present. A gap may be located between the regulation zone and the blocking zone on the test strip. In such an embodiment, the second gap is shorter than the first gap. Therefore, the time period in which the liquid sample contacts the analyte binding zone for reacting with the analyte binding antibodies is longer than the time period in which the sample contacts the ligands. The binding between the analyte binding antibody and the analyte in the liquid sample is more complete than the binding between the ligands and the analyte antibodies in the second liquid mixture due to the different lengths in times.

Figure 2A:
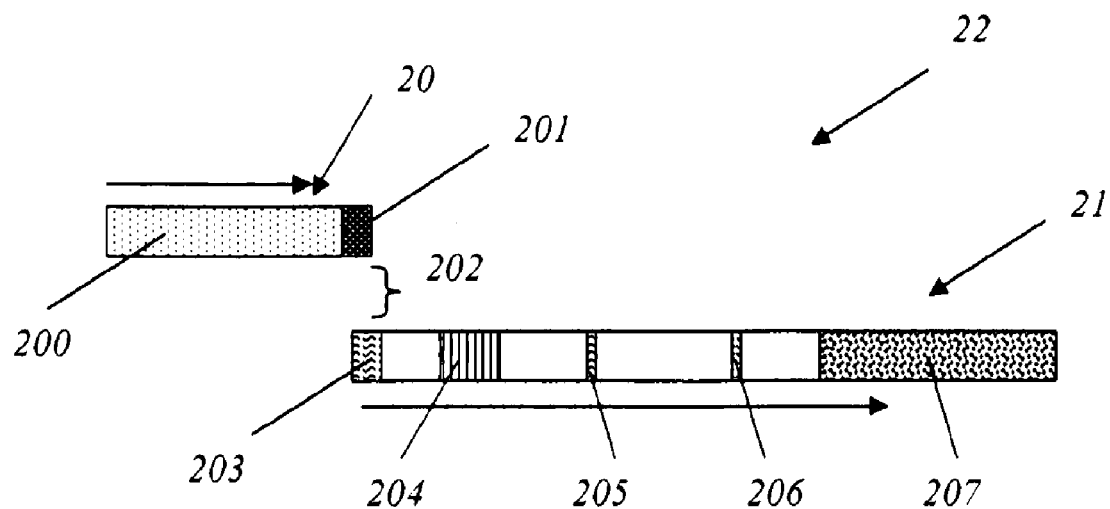
FIGS. 2A & 2B illustrate a test strip of the device comprising two strips separated by a vertical distance.
Figure 2B:
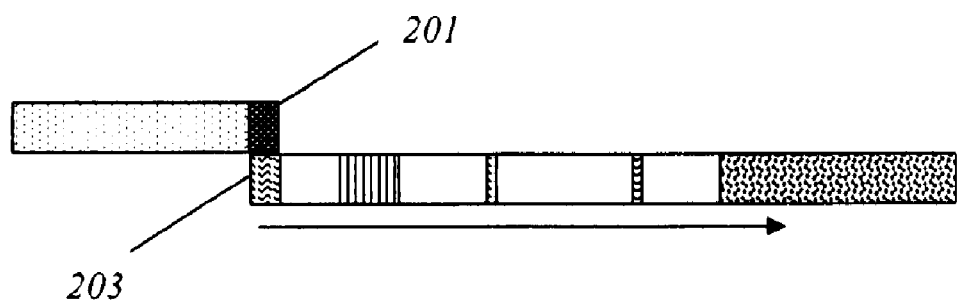

In another aspect of the device described herein, a vertical distance is present between the antibody and the ligand as shown in FIG. 2A. In such an embodiment, the analyte binding zone 201 is located on a first piece of bibulous strip 20 and the regulation zone 203 is located on a second bibulous strip 21. A gap 202 exists between the two strips 20, 21. The first strip 20 is typically positioned above, and is physically separated from, the second strip 21. The first strip can be located in any suitable position relative to the second strip, so long as the first and second strips are physically separated. A sample is applied to the device at the sample application zone 200 located on the first strip 20. The sample contacts the first strip 20 and dissolves the analyte binding antibodies in the analyte binding zone 201 into a liquid phase to form a first analyte-antibody mixture. The mixture can be maintained in the analyte binding zone for a period of time. The first strip 20 is then positioned adjacent to, and in fluid communication with, the second strip 21, as shown in FIG. 2B. The sample flows from the first strip 20 to the second strip 21 through the analyte binding zone 201 to the regulation zone 203 when the first strip 20 is in contact with the second strip 21. After contact occurs between the first and second strips 20, 21, the analyte-antibody mixture comes into contact with the regulation zone 203 located on the second strip 21. The antibody-analyte mixture further dissolves the ligands contained on the regulation zone 203 so as to form a second mixture. The second mixture is typically formed in a time period shorter than the time period in which the first mixture was formed.

A blocking zone 204 is typically located downstream from the regulation zone 203 in the detection device. The second liquid mixture in the regulation zone then flows along the length of the test strip to the blocking zone. In an alternative embodiment the first strip is already in fluid communication with the second strip. In such an embodiment, the liquid mixture can automatically drop down to arrive in the regulation zone 201 due to the gravitation of the liquid sample.

In some embodiments, an amount of trapping receptors are immobilized on the blocking zone. The immobilized trapping receptors have specific sites for binding the ligand but do not directly binding any of the analyte-binding antibodies in the second liquid mixture. The trapping receptors can be selected from an antibody, an antibody fragment, one partner of some specific molecule pairs irrelevant to the mobilizeable ligand, or any other suitable trapping receptor. When one partner of a pair of specific molecules is immobilized on the blocking zone, another partner of the pair of specific molecules can be conjugated with the ligand and contained on the regulation zone. The specific molecule pairs can be selected from biotin and avidin, biotin and streptavidin, antibody and an antigen (antibody for binding a target analyte and analyte itself are excluded), rhodamine and anti-rhodamine, mouse IgG and anti-mouse IgG, or any other suitable molecular pair. More particularly, if the mobilizeable ligand are attached or labeled or bound with biotin in the mobilization zone, the blocking zone immobilizes the ligands by an amount of avidin for specifically binding the biotin, as a portion of a conjugate conjugated with the ligands.

In another embodiment, the mobilizeable ligand (antigen-ligand) is conjugated with a protein. Generally, one protein molecule can be conjugated with several small antigens so that monomolecular antigen ligand can bind to several receptors for the analyte. The antigen ligand can also link with biotin. In negative condition, the antigen ligand reacts with the analyte antibody to form a complex (analyte-antibody-biotin complex). When the complex moves to the solid phase with liquid flowing and binds to streptavidin-IgG complex, one monomolecular streptavidin-IgG complex can bind to four molecular biotin. This multi-site conjugation prevents the analyte and antibody from moving past the solid phase. The ability to prevent as few as possible antibodies or analytes accordingly decreases the possibility of false positive. Other reagents for improving the test can also be disposed on or upstream of the blocking zone. In addition, the blocking zone in some embodiments is disposed on a solid material including, but not limited to, filter paper, cellulose membranes, nylon membranes, or any other suitable material. In some embodiments, the blocking zone is disposed on a cellulose membrane.

Figure 3A:
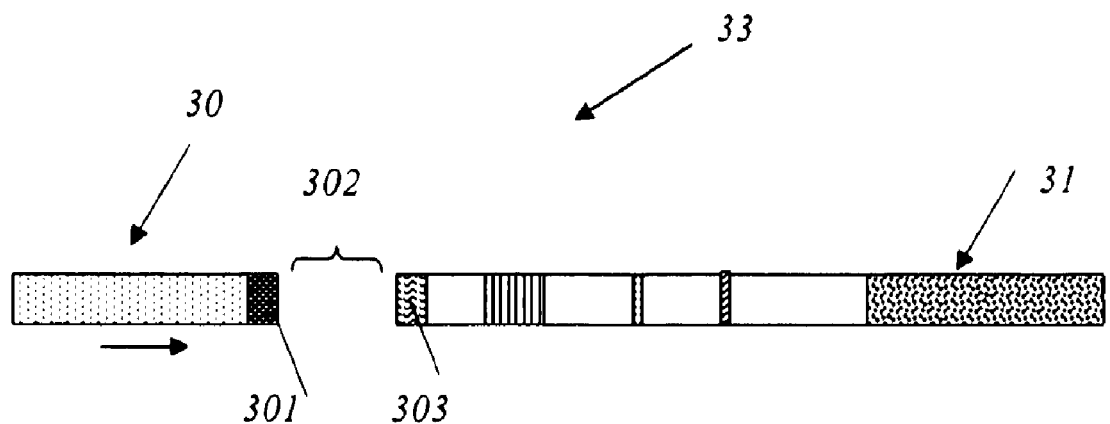
FIGS. 3A & 3B illustrates an alternative embodiment of a test strip having two portions separated by a horizontal distance.
Figure 3B:
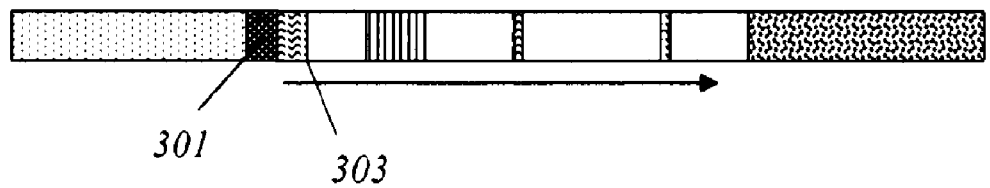

A device in which a horizontal gap is present between the analyte binding zone 301 and the regulation zone 303 is shown in FIG. 3A. The analyte binding zone 301 is located on a first strip 30, and the regulation zone 301 is contained on a second strip 31. The first strip 30 is separated from the second strip 31 along the horizontal axis by a gap 302 between the two strips. The sample is applied to the first strip 30 at the sample application zone. The sample comes into contact with the analyte binding zone 301 on the first strip 30. The antibodies located in the analyte binding zone 301 are then dissolved into the sample and a first sample mixture is formed. The first sample mixture can be maintained in the analyte binding zone for a period of time. The first strip 30 can then be positioned adjacent to the second strip 31, as shown in FIG. 3B. When the analyte binding zone 301 is placed in fluid communication with the regulation zone 303, the sample flows from the analyte binding zone 301 to the regulation zone, wherein a second liquid mixture is formed. The gap between the analyte binding zone 301 and the regulation zone 303 can be designed to meet various requirements, including, but not limited to, the particular sensitivity and specificity requirements for testing one target analyte using the present device. In some embodiments, the width of the gap 302 is between about 1 and 100 millimeters. In some embodiments, the width of the gap is at least 1, 1, 2, 3, 4, 5, 6, 7, 8, 9 or 10 millimeters. In some embodiments, the gap is more than 100 millimeters.

Figure 4:
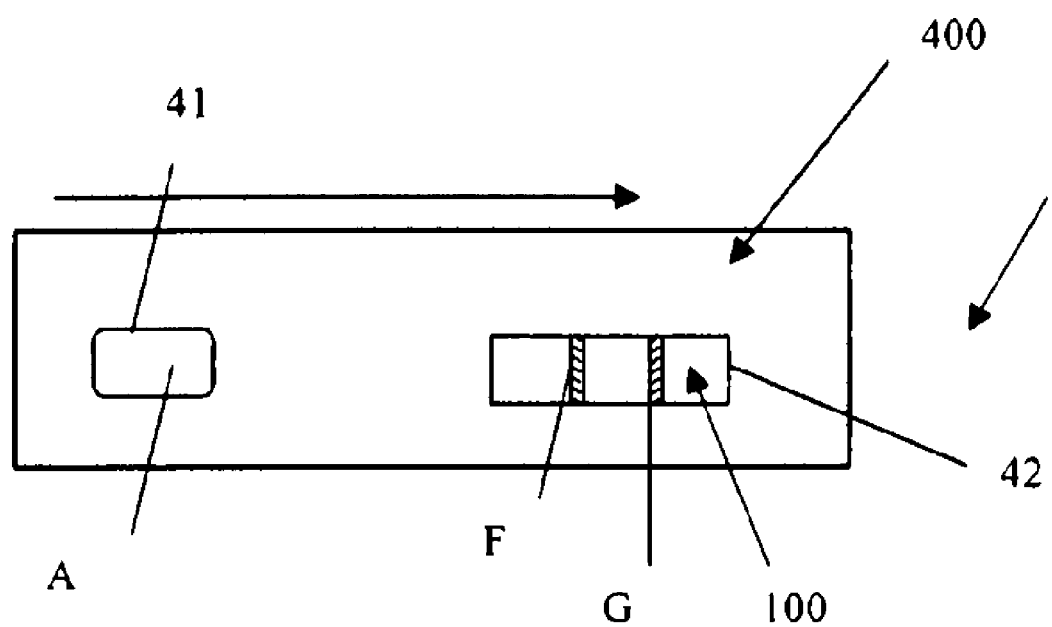
FIG. 4 illustrates a device having a housing for the test strip.

In some embodiments, the test device has a housing 400 for housing the test strip 100, as depicted in FIG. 4. The housing 400 comprises a sample well 41, through which a sample is introduced to the strip 100. As illustrated FIG. 4, the housing 400 has a sample well 41 aligned with the sample application zone A, and a window 42 aligned with the detection zone F and the control zone G. The result shown on the detection zone F can be read through the transparent viewing window 42. The blocking zone D and mobilizeable zone K (as seen in FIG. 1) are typically hidden by the opaque wall of the housing. In some embodiments, the blocking zone and the mobilization zone are viewable through the device wherein the walls of the device are transparent.

II. METHODS

Also provided herein are methods for using the test device. One method for using the test device comprises detecting the presence or absence of a target analyte in a liquid sample with a direct positive or negative result. The method includes contacting a sample with an amount of analyte binding antibodies for specifically binding target analytes or an amount of ligand so as to form a first liquid mixture. The first mixture contains antibody-analyte complexes if the target analyte is present. The first liquid mixture further contains an amount of antibodies if the amount of analyte is less than the amount of the antibodies or an amount of analyte if the amount of analyte is more than the amount of the antibodies. The first mixture is typically incubated or maintained for a first time period prior to coming into contact with an amount of ligand, so as to form a second liquid mixture. The ligands in the second liquid mixture compete with the analyte for binding the antibodies of the antibody-analyte complexes in a substantially liquid phase. The second liquid mixture is typically incubated or maintained a second time period, the second time period being shorter than the first time period. During the second time period the second liquid mixture contacts the solid phase with a blocking zone having an amount of trapping receptors for extracting the ligands, including the unbound ligands or the ligand-antibody complexes, from the second liquid mixture. The analyte-binding antibodies are not directly bound in this second liquid mixture. The test result correlates to the amount of antibody-analyte complexes.

In other embodiments, the method includes applying a liquid sample to a solid phase comprising an analyte binding zone, a regulating zone separated from and downstream from the analyte binding zone, a blocking zone and a detection zone. An amount of analyte binding antibodies is contained on the analyte binding zone in a dry state. An amount of ligands is contained on the regulation zone in a dry state. The analyte binding antibodies and the ligands can be dissolved in a liquid phase and carried by a liquid sample. The blocking zone contains an amount of immobilized trapping receptors for binding the ligands but not binding any analyte-binding antibody directly.

Also provided herein are methods for detecting the presence or absence of an analyte. One method for detecting the presence or absence of an analyte in a sample comprises contacting the sample with an amount of antibody for specifically binding an amount of either a target analyte or a ligand as to form a first mixture; contacting the first mixture with an amount of ligand to form a second mixture; contacting the second mixture to a solid phase comprising a blocking zone, wherein the blocking zone comprises an amount of immobilized trapping receptors specifically binding the ligands but not directly binding the antibodies of the first mixture; and determining the amount of the antibodies in the second mixture, wherein the amount of antibodies detected corresponds to an amount of the analyte in the liquid sample. In some embodiments, the solid phase comprises a lateral flow strip. In some embodiments, both the ligands and the antibodies for binding the analytes are dried on the lateral flow strip and disposed upstream of the blocking zone. The method can further provide for the formation of a molecular conjugate comprising a ligand unrelated to the analyte and the trapping receptor is formed in the second mixture. The molecular conjugate can be selected from biotin and avidin, biotin and streptoavidin, or rhodamine and anti-rhodamine. Additionally, the molecular conjugate further comprises a detectable label. The detectable label can be selected from the group consisting of colloidal gold, a latex particle, or a chromophore. In some embodiments an affinity constant between the mobilizeable antibody and the mobilizeable ligand is higher than an affinity constant between the analyte and the mobilizeable antibody is present. In some embodiments, the length of time in which the sample contacts the analyte binding antibodies is longer than the length of time in which the first liquid mixture contacts the ligands.

III. EXAMPLES

The invention will be further illustrated by the following examples, which are intended to be purely examples of the invention and not as limitations to the invention.

Example 1

Detection of Cocaine in Urine

Preparing a Conjugated with Cocaine Antibody Conjugated with Colloidal Gold

3 L of a colloidal gold solution, having symmetrical and suitable particles (20-40 nm in diameter), was prepared in a clean glass container. The colloidal gold solution was first mixed. A phosphate buffer solution with a pH=7.0 was then added to the colloidal gold solution to adjust the pH of the colloidal gold solution to about 6.8. 25 mg of COC monoclonal antibody was then added to the mixture. The solution was continually mixing for approximately 1 hour. After mixing the solution, 35 ml of 10% BSA was added to block the reaction. The solution was then mixed again for an additional hour. In succession, the block solution was then centrifuged at 11000 rpm for 35 minutes. The supernatant was then removed. Afterward, the deposition was dissolved in 0.003 mol/L 0.02% BSA/phosphate solution (washing buffer), and the solution centrifuged again. The supernatant was decanted again and the deposition collected. Thereafter, the concentration of the colloidal gold solution can then be adjusted as needed. The OD value of the solution under 540 nm wavelength was then determined.

Preparing a Conjugate with Cocaine and Biotin (COC-BSA-Biotin)

2.5 mg/ml of BSA-Cocaine conjugate (purchased from Immunetic, Inc) was dialyzed in 1000 ml NaHCO$_3$ buffer solution (pH=8.0) for 4 hours to form solution (1). After diluting biotin with distilled water to a concentration of 10 mM, 47 μl biotin solution and solution (1) were mixed together and stirred for 1 hour at room temperature to form the solution (2). Determining that the solution (2) was dialyze in 1000 ml phosphate buffered solution (pH=7.4) for 12 hours to and from solution (3). The concentration of cocaine-BSA-Biotin under 655 nm wavelengths in a spectrophotometer, was then diluted into solution (4) to form the terminal solution in concentration of 0.5 mg/ml.

Preparation of the Test Strip

A test strip as shown in FIG. 1 was prepared.

Preparation of the sample application pad: A sample application pad M made from fiberglass was used. The fiberglass was then treated with buffered solution (Borax 0.05M, pH9.3, surface active reagent: 2% S-17: (RHODASURF®ON-870)) and dried in oven at 37° C.

Preparation of label pad B: The polyester membrane was then treated with a buffered solution (PVA 5 g/L, Na$_2$HPO$_4$, 7.1 g/L, S-14 (Triton-X-100) 0.1%, BSA 5 g/L, NaN$_3$ 0.2 g/L). The membrane was dried in the oven at 37° C. The membrane was additionally treated with anti-COC labeled with colloidal gold particles under the concentration of 10 OD and in the condition of 1 ul/cm and automatic spray microprocessor, to form label pad 1. Label pad 1 was then dried in oven at 37° C.

Preparation of label pad C: The polyester membrane was treated with buffered solution (PVA 5 g/L, Na$_2$HPO$_4$, 7.1 g/L, S-14 (Triton-X-100) 0.1%, BSA 5 g/L, NaN$_3$ 0.2 g/L) and was dried in oven at 37° C. The membrane was then treated with 0.5 mg/ml Biotin-BSA-COC solution 4 under the criterion of 2.5 ul/cm and automatic spray microprocessor to form label pad 2. Label pad 2 was then dried in oven at 37° C.

Preparation of the nitrocellulose membrane: The blocking zone D of the nitrocellulose (NC) membrane E was treated with Streptavidin-IgG (Yingkelong Biotechnology (Hangzhou) Co., Ltd.) at a concentration of 0.6 mg/ml and in the condition of 2.5 ul/cm and 3 bands automatic spray microspray-membrane processor. The detection zone F was treated with goat anti-mouse antibody IgG (purchased from Fitzgerald Inc) at a concentration of 0.6 mg/ml and in the criterion condition of 1.0 ul/cm and 1 bands automatic spray microspray-membrane processor. Thereafter, the NC membrane E was dried in an oven at 37° C.

Construction of the test strip with sample pad, labeled pads, and NC membrane: The prepared parts were cut into a test strip of approximately 0.4×10 cm. The sample application zone A, label pad 1 B, label pad 2 C, NC membrane E and absorbent filter paper H were sequentially assembled. Label pad 1 B and label pad 2 C remained isolated from the sample application zone A, label pad 1 B, label pad 2 C, and the NC membrane E by a distance 102. All these parts were adhibited onto a bibulous material.

Dilution of Cocaine Detection Solution

Dilute cocaine with the negative urine into detection solution under the concentration of 0 ng/ml, 150 ng/ml, 50 ng/ml, 100 ng/ml, 150 ng/ml, 450 ng/ml and 900 ng/ml.

The detection results are summarized in Table 1.

TABLE 1

| Cocaine detection solution | quantity | Result Negative | positive | exact quantity | exact incident |
|---|---|---|---|---|---|
| negative detection solution | 10 | 10 | 0 | 10 | 100% |
| 25 ng/ml | 10 | 5 | 5 | 5 | 50% |
| 50 ng/ml | 10 | 0 | 10 | 10 | 100% |
| 100 ng/ml | 10 | 0 | 10 | 10 | 100% |
| 150 ng/ml | 10 | 0 | 10 | 10 | 100% |
| 450 ng/ml | 10 | 0 | 10 | 10 | 100% |
| 900 ng/ml | 10 | 0 | 10 | 10 | 100% |

Figure 5:
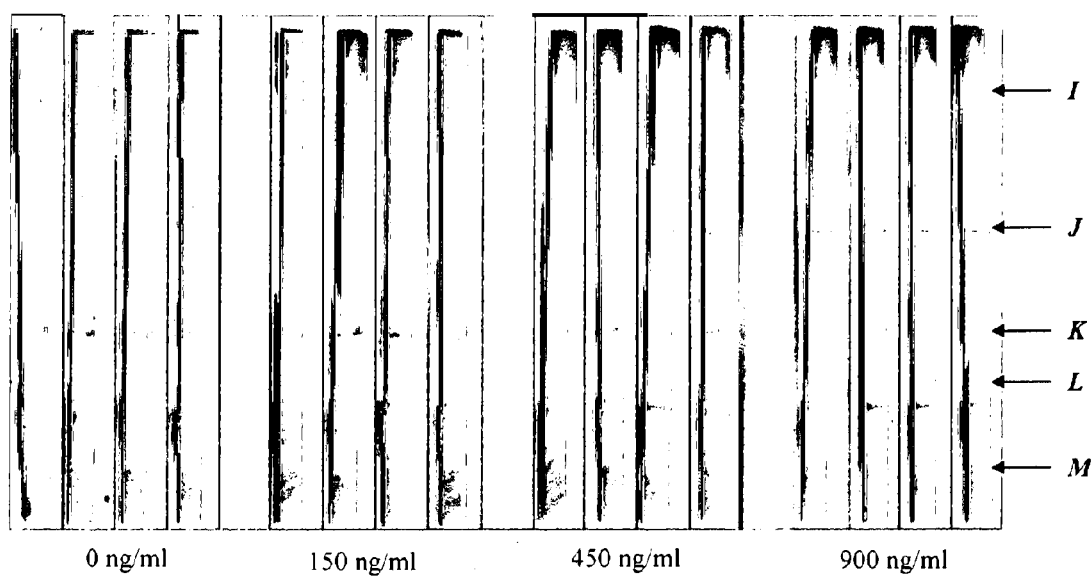
FIGS. 5A-5F illustrate the results displayed by the device in detecting different analytes.

The result for the cocaine test strip is shown in FIG. 5A. The test shows the results in the detection zone J for different concentrations of cocaine in the urine samples. The cocaine concentrations of the sample are 0 ng/ml, 150 ng/ml, 450 ng/ml and 900 ng/ml from left to right. I: absorption zone; J: detection zone; K: blocking zone; L: labeled zone; M: sample reception zone.

Analysis of Result:

The detection result shows that detection sensitivity can be improved up to 50 ng/ml degree following the method and the device provided by present invention. False-negatives were not found.

Example 2

Detection of Phencyclidine (PCP) in Urine

A test strip was prepared as described in Example 1. The protocol followed was the same as Example 1 with several differences: (1) COC was replaced with PCP; (2) buffered solution for treating sample application pad A was TRIS buffered solution, the concrete prescription including 0.1M TRIS salt (PH=8.0), surface active reagent comprising 1% S-7 (RHODASURF®ON-870), 1% S-9 (RHODASURF®ON-870) and 1% BSA; (3) the concentration of Biotin-BSA-PCP for treating label pad C was 1 mg/ml, the treating criterion is 2.5 ul/cm, and the label pad C was dried in oven at 37° C.; (3) when preparing the NC membrane E, the detection result operation zone G, which is downstream from detection zone F and near absorbent pad H, is coated with goat anti-rabbit IgG. The coating method is the same as that for detection zone F in Example 1.

Dilution of PCP solution: Dilute PCP with negative urine into detection solution under the concentration of 0 ng/ml, 12.5 ng/ml, 37.5 ng/ml and 75 ng/ml.

Label pad 1 was treated with rabbit IgG and colloidal gold particles under the concentration of 0.6 mg/ml and automatic spray microprocessor. Thereafter, the label pad 1 was dried in oven at 37° C. The concentration and method of other reagents are the same as in Example 1.

Figure 5B:
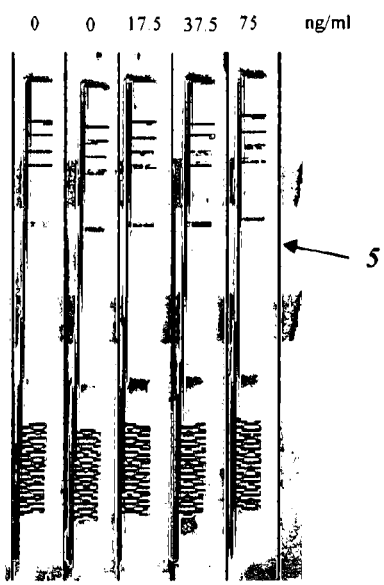

Detection Result:

FIG. 5B illustrates how when PCP is not present in the urine sample, no band appears in the detection zone 5, which indicates a negative result directly (first and second from left to right). When PCP is present, a band appears in the detection zone, and the band color darkens as the concentration increases.

Example 3

Detection of Methyl-amphetamine (MET) in Urine

The test strip procedure used is the same as that described in Example 1. The protocol followed is similar to that described in Example 2 with the exception that PCP is replaced with methyl-amphetamine (MET), where the MET dilution is achieved by diluting MET with the negative urine into the detection solution with concentration 0 ng/ml, 150 ng/ml, 450 ng/ml, and 900 ng/ml.

Figure 5C:
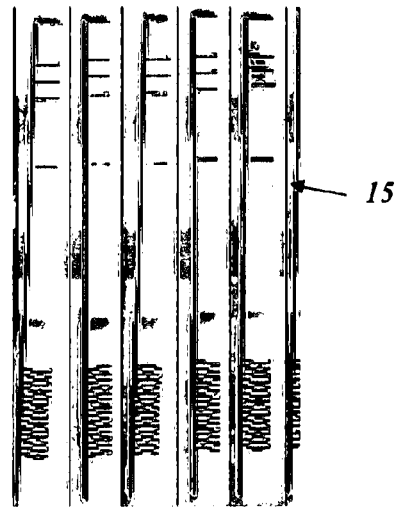

Detection Result:

FIG. 5C illustrates how when MET is not present in the urine sample, no band appears in the detection zone 15, which indicates a negative result directly (first and second from left to right). When MET is present, a band appears in the detection zone, and the band color darkens as the concentration increases.

Example 4

Detection of Morphine in Urine

The test strip procedure used is the same as that described in Example 1. The protocol followed is similar to that described in Example 2 with the exception that PCP is replaced with morphine. The morphine dilution solution is created by diluting MOP with the negative urine into a detection solution with concentration 0 ng/ml, 105 ng/ml, 450 ng/ml, and 900 ng/ml.

Figure 5D:
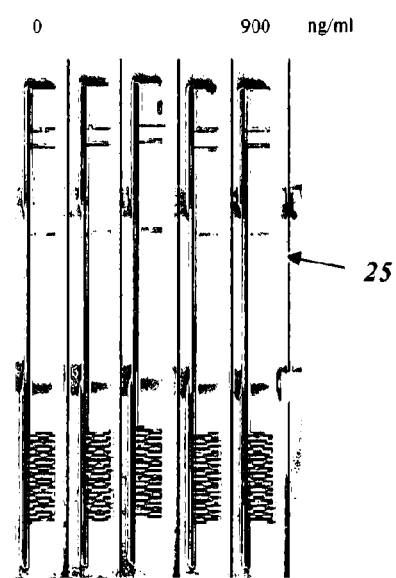

Detection Result:

FIG. 5D illustrates how when MOP is not present in the urine sample, no band appears in the detection zone 25, which indicates a negative result directly (first and second from left to right). When MOP is present, a band appears in the detection zone, and the band color darkens as the concentration increases.

Example 5

Detection of Amphetamine (AMP) in Urine

The test strip procedure used is the same as that described in Example 1. The protocol followed is similar to that described in Example 2 with the exception that PCP is replaced with amphetamine (AMP). The AMP dilution is created by diluting AMP with the negative urine into a detection solution with concentration 0 ng/ml, 150 ng/ml, 1500 ng/ml, and 3000 ng/ml.

Figure 5E:
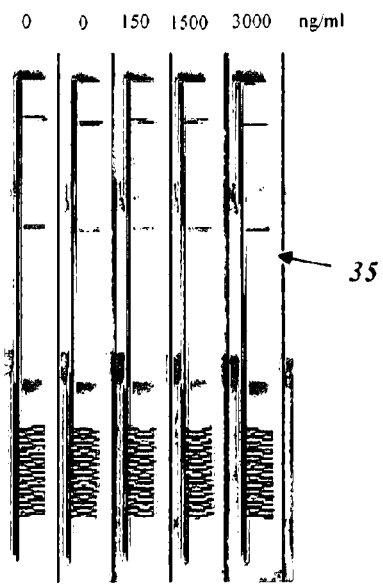

Detection Result:

FIG. 5E illustrates how when AMP is not present in the urine sample, no band appears in the detection zone 35, which indicates a negative result directly (first and second from left to right). When AMP is present, a band appears in the detection zone, and the band color darkens as the concentration increases.

Example 6

The Detection of Tetrahydrocannabinol (THC) in Urine

The test strip procedure used is the same as that described in Example 1. The protocol followed is similar to that described in Example 2 with the exception that PCP is replaced with tetrahydrocannabinol (THC). The THC dilution is created by diluting THC with the negative urine into detection solution with concentration 0 ng/ml, 17.5 ng/ml, 75 ng/ml, and 150 ng/ml.

Figure 5F:
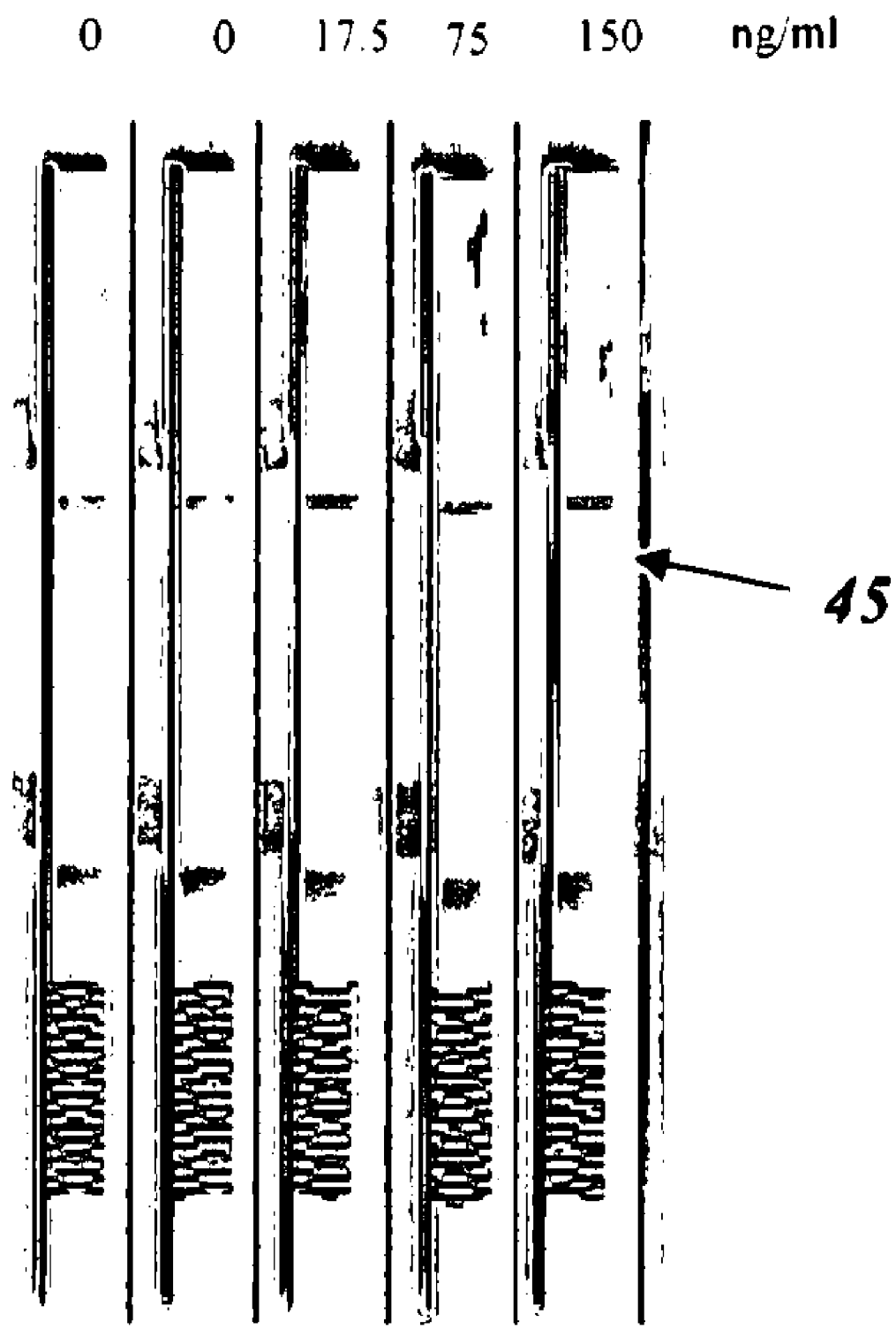

Detection Result:

FIG. 5F illustrates how when THC is not present in the urine sample, no band appears in detection zone 45, which indicates a negative result directly (first and second from left to right). When THC is present, a band appears in the detection zone, and band color darkens as the concentration increases.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A test device for detecting the presence or absence of an analyte in a liquid sample comprising:
   a) a mobilization zone comprising a mobilizeable ligand and a mobilizeable antibody, the mobilizable antibody being capable of specifically binding the analyte and the mobilizeable ligand non-simultaneously, wherein the mobilizeable antibody and the analyte exhibit a binding affinity greater than that of the mobilizeable antibody and the mobilizeable ligand, and wherein the mobilizeable antibody is contacted by the sample before the mobilizeable ligand is contacted by the sample;
   b) a blocking zone located downstream from the mobilization zone, wherein the blocking zone comprises an immobilized trapping receptor that binds the mobilizeable ligand; and
   c) a detection zone located downstream from the blocking zone, wherein the detection zone comprises an immobilized detecting receptor that binds the mobilizeable antibody.

2. The device of claim 1 wherein the mobilizeable ligand is spatially separated from the mobilizeable antibody so that the sample contacts the mobilizeable antibody prior to contacting the mobilizeable ligands.

3. The device of claim 1, wherein the mobilization zone, the blocking zone, and the detection zone define a lateral flow strip format.

4. The device of claim 1, wherein the mobilizeable ligand and the mobilizeable antibody are separated by a gap.

5. The device of claim 1 wherein the mobilizeable ligand comprises a member of a binding pair that is distinct from the analyte, and wherein the immobilized trapping receptor comprises other member of the binding pair.

6. The device of claim 5, wherein the binding pair is selected from the group of biotin and avidin, biotin and streptoavidin, and rhodamine and anti-rhodamine.

7. The device of claim 5, wherein the binding pair consists of biotin and streptoavidin.

8. The device of claim 1, wherein the mobilizeable ligand and the mobilizeable antibody are separated from each other by a vertical distance.

9. The device of claim 1, wherein the mobilizeable ligand and the mobilizeable antibody are separated from each other by a horizontal distance.

10. The device of claim 1, wherein the mobilizeable antibody exists in a dry state and is contained in a first bibulous strip, and the mobilizeable ligand exists in a dry state and is contained in a second bibulous strip; and wherein the first strip is physically separated from the second strip.

11. The device of claim 10, wherein the blocking zone and detection zone are located on the second bibulous strip, downstream from the mobilizeable ligand.

12. The device of claim 1 wherein the mobilizeable antibody further comprises a color particle.

13. The device of claim 1, wherein the mobilizeable ligand and mobilizeable antibody are configured on the mobilization zone so that contact time during which the sample contacts the mobilizeable antibody is longer than contact time during which the sample contacts the mobilizeable ligand.

14. The device of claim 1, wherein the mobilizeable antibody comprises a detectable label.

15. A method for detecting the presence or absence of an analyte in a liquid sample comprising: contacting the liquid sample with a test device of any one of claims 1-11 and 12-14 thereby detecting the presence or absence of said analyte.

16. The method of claim 15, wherein the liquid sample is permitted to first contact mobilizeable antibody on the test device to form a first mixture, followed by contacting the first mixture with the moblizeable ligand to form a second mixture, wherein the second mixture further makes contact with the blocking zone.

17. The method of claim 15, wherein the test device is a lateral flow strip.

18. The method of claim 17, wherein both the ligands and the antibodies exist in dry state on the lateral flow strip.

19. The method of claim 15, wherein the mobilizeable ligand comprises a member of a binding pair that is distinct from the analyte, and wherein the immobilized trapping receptor comprises other member of the binding pair.

20. The method of claim 19, wherein the mobilizeable antibody comprises a detectable label.

21. The method of claim 20, wherein the detectable label is selected from the group consisting of an enzyme, colloidal gold, latex particle, and chromophore.

22. The method of claim 15, wherein the binding pair is selected from the group of biotin and avidin, biotin and streptoavidin, and rhodamine and anti-rhodamine.

23. The method of claim 15, wherein the mobilizeable ligand and mobilizeable antibody are configured on the mobilization zone so that contact time during which the sample contacts the mobilizeable antibody is longer than contact time during which the sample contacts the mobilizeable ligand.

* * * * *